(12) United States Patent
White et al.

(10) Patent No.: US 7,704,746 B1
(45) Date of Patent: Apr. 27, 2010

(54) METHOD OF DETECTING LEAKAGE FROM GEOLOGIC FORMATIONS USED TO SEQUESTER $CO_2$

(75) Inventors: Curt White, Pittsburgh, PA (US); Arthur Wells, Bridgeville, PA (US); J. Rodney Diehl, Pittsburgh, PA (US); Brian Strazisar, Venetia, PA (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 12/351,348

(22) Filed: Jan. 9, 2009

Related U.S. Application Data (63) Continuation-in-part of application No. 10/845,611, filed on May 13, 2004, now abandoned.

(51) Int. Cl.
*G01N 37/00* (2006.01)
(52) U.S. Cl. .............................. 436/56
(58) Field of Classification Search ............ 436/56
See application file for complete search history.

(56) References Cited

U.S. PATENT DOCUMENTS 2,578,500 A * 12/1951 Savoy et al. ............ 436/27
5,767,390 A *  6/1998 Chapman, IV .......... 73/40.7

OTHER PUBLICATIONS

Anderson, R. P.; Vogh, J.W. "Various tracers identify injected storage gas." Oil Gas J. 1989, vol. 87, pp. 52-54, & 56.*
Simmonds, P.G.; Greally, B.R.; Olivier, S.; Nickless, G.; Cooke, K.M.; Dietz, R.N. "The background atmospheric concentrations of cyclic perfluorocarbon tracers determined by negative ion-chemical ionization mass spectroscopy." Atmospheric Environment, 2002, vol. 36, pp. 2147-2156.*
Klusman, R. "Evaluation of leakage potential from a carbon dioxide EOR/sequestration project." Energy Conversion and Management, 2003, 44, pp. 1921-1940.*
Knox, P. R.; Paine, J. G.; Hovorka, S. D. Optimal Geological Environments for Carbon Dioxide Disposal in Brine Formations (Saline Aquifers) in the United Stated- Pilot Experiment in the Frio Formation, Houston Area. DOE/EA-0000(Draft), Apr. 2003.*

* cited by examiner

*Primary Examiner*—Walter D Griffin
*Assistant Examiner*—Bobby Ramdhanie
(74) *Attorney, Agent, or Firm*—Joy Alwan; Brian J. Lally; Paul A. Gottlieb (57) ABSTRACT

The invention provides methods for the measurement of carbon dioxide leakage from sequestration reservoirs. Tracer moieties are injected along with carbon dioxide into geological formations. Leakage is monitored by gas chromatographic analyses of absorbents. The invention also provides a process for the early leak detection of possible carbon dioxide leakage from sequestration reservoirs by measuring methane ($CH_4$), ethane ($C_2H_6$), propane ($C_3H_8$), and/or radon (Rn) leakage rates from the reservoirs. The invention further provides a method for branding sequestered carbon dioxide using perfluorcarbon tracers (PFTs) to show ownership.

9 Claims, 9 Drawing Sheets

METHOD OF DETECTING LEAKAGE FROM GEOLOGIC FORMATIONS USED TO SEQUESTER $CO_2$

CROSS-REFERENCE TO RELATED APPLICATION

This application is a continuation-in-part of U.S. application Ser. No. 10/845,611 filed May 13, 2004 now abandoned.

CONTRACTUAL ORIGIN OF INVENTION

The United States Government has rights in this invention pursuant to an employer-employee relationship between the U.S. Department of Energy and the inventors.

BACKGROUND OF THE INVENTION

1. Field of the Invention

This invention relates to a method to determine carbon dioxide ($CO_2$) leaks from sequestration reservoirs, and, more specifically, this invention relates to an improved and enhanced method for the detection and quantification of leaks of carbon dioxide from geologic formations.

2. Background of the Invention

Carbon dioxide is a greenhouse gas, yet is useful for the manufacture of such chemicals as carbonates. Sequestration of $CO_2$, produced from fossil fuel-fired electric power generating facilities and other stationary sources is an essential part of this country's efforts to reduce greenhouse gas emissions. In June 2003 the United States signed a charter with the European Union's Executive Commission and twelve countries including Russia, China, Japan, Canada, and Brazil to research the technology for storage of carbon dioxide in geologic formations.

Approximately 7.4 Giga tons (Gt) of carbon dioxide are emitted annually from all fossil fuel emission sources such as automobiles, powerplants, and industrial facilities. About 25% of the 7.4 Gt are sequestered by terrestrial ecosystems, e.g., forests and agricultural plants. Less than 0.01% of the 7.4 Gt is intentionally sequestered.

United States policy may mandate carbon dioxide sequestration in geologic repositories. Exemplary repositories include active and depleted oil and gas wells, saline aquifers, salt domes, and deep, often unmineable coal deposits. Potential leaks from such repositories must be monitored.

The problem of substantiating, monitoring, and verifying the long-term storage integrity of carbon dioxide sequestered in underground reservoirs is complicated by the fact that the reservoirs may be very deep, sometimes greater than 5000 feet. Many reservoirs are covered by seemingly impenetrable rock strata. While many geologists believe that reservoirs are permanently sealed by cap rock strata, evidence exists that shows micro seepage can be a long-term factor. Accordingly, a need exists to determine if the carbon dioxide is effectively sequestered or moving vertically through or around a cap rock or laterally along a cap rock. This determination will help verify the integrity of physical barriers to the escape of carbon dioxide.

Direct determination of carbon dioxide leakage from the sequestration reservoir to the atmosphere is rendered difficult by the presence of atmospheric carbon dioxide. Further, atmospheric carbon dioxide's concentration is high and seasonally variable. The high concentration makes difficult the detection of micro seepage of carbon dioxide by simple measurement of carbon dioxide in the atmosphere above the sequestration reservoir. The seasonal variation would require that baseline determinations of atmospheric carbon dioxide concentration be frequently made.

In addition, carbon dioxide is often pumped into oil reservoirs to enhance oil recovery (EOR) and well yield. A method that can monitor carbon dioxide movement could provide information about the underground flow of fluids to improve such oil recovery techniques.

Further, some leaks can be intermittent. A breach of the natural seal between the storage area and higher strata can occur. That breach may be only temporary. For example, a certain quantity of $CO_2$ may be released until the pressure on the overburden strata is reduced and the sequestration reservoir reseals itself. Pressure buildup and release may be a sporadic process, and any tracers used could be quickly dispersed. Continuous monitoring using ground-based systems would offer the ability to detect even sporadic intermittent leaks.

Carbon dioxide, when pumped into a geological formation, causes gases such as methane ($CH_4$), ethane ($C_2H_6$), propane ($C_3H_8$), and radon (Rn) to desorb from the formation. Experience at EOR sites shows that concentrations of these gases immediately above reservoirs are known to respond quickly to well operations such as pumping rates, reservoir flooding, and over-pressurization of the reservoir. As such, increased surface flux and/or concentrations of these gases in soil gas can be monitored as an indicator of carbon dioxide leakage. Measurement of light hydrocarbon concentrations in the soil above a sequestration reservoir as a means for monitoring carbon dioxide leakage has been proposed. This is discussed in: R. W. Klusman, "Evaluation of Leakage Potential from a Carbon Dioxide EOR/Sequestration Project," *Energy Conversion and Management*, 44, 1921-1940 (2003).

In any reservoir leak scenario, carbon dioxide displaces methane and other gases from any geological media onto which the methane and other compounds are sorbed. Thus, methane moves ahead of carbon dioxide. In a subsurface environment, methane, ethane, propane, and radon are more mobile because they are less adsorptive and less water-soluble than carbon dioxide. Increased amounts of methane, other light hydrocarbons, and Rn at or near the surface of a sequestration reservoir suggests a leak pathway from the reservoir to the surface. Sequestration into that particular geological formation should then be reconsidered. If methane and other light hydrocarbons from the sequestration formation can leak to the surface, so can carbon dioxide.

In the alternative, tracer molecules can be injected with the carbon dioxide into sequestration reservoirs. Radioactive tracers have been used extensively in the past, but regulation and public opinion have discouraged their use. Halogen- and/or sulfur-containing compounds can serve well as tracers. These compounds have very low background levels in the atmosphere, and can be determined at low levels using conventional gas chromatographic analysis with electron capture or photo-ionization detectors, or combined gas chromatography-mass spectrometry.

Tracers should have a high level of detectability, be free from significant background interference, have a similarity to carbon dioxide in migration and chemical characteristics, be chemically stable, be safe and environmentally benign, and be relatively non-corrosive. Also, tracer cost in bulk will be an important consideration inasmuch large amounts of the tracers may be needed to spike an underground reservoir. Several tracers can be employed simultaneously, each with its own unique advantages and limitations.

Perfluorocarbon (PFTs) tracers have been tested and shown to be an effective means to evaluate barrier integrity, as shown in T. M. Sullivan, J. Heiser, A. Gard, and G. Senum, "Monitoring Subsurface Barrier Integrity Using Perfluorocarbon Tracers," *Journal of Environmental Engineering*, 124 (6) (June) 490-497 (1998).

PFTs have been used to locate and quantify leaks in water cooled stator bars in nuclear power plant generators. Conventional detection methods for PFTs include collection of the leaking PFTs on sorbents with subsequent gas chromatographic-electron capture detection.

U.S. Pat. No. RE36,951 awarded to Cooper, et al. on Nov. 14, 2000 discloses the use of a leak detection dye in climate control systems.

U.S. Pat. Nos. 6,070,455 and 5,681,984 awarded to Cavestri on Jun. 6, 2000, and Oct. 28, 1997, respectively, disclose the use of a leak detecting dye in climate control systems. The dye is absorbed onto a non-absorbent carrier.

U.S. Pat. No. 5,143,568 awarded to Sheahan on Sep. 1, 1992 discloses a leak detection method using a tracer gas to test the integrity of roofing seams.

U.S. Pat. No. 4,755,757 awarded to Cooper on Jul. 5, 1988 discloses a fluid leak detection system for determining the rate of fluid leakage through a geomembrane.

None of the aforementioned patents disclose a method for detection of carbon dioxide leakage from a sequestration reservoir. In particular, a method to account for background/soil/bacteria sources of carbon dioxide is not disclosed.

A need exists in the art for a method of detection of carbon dioxide leakage from sequestration reservoirs. The method should account for background carbon dioxide sources when engaging in carbon dioxide leak detection from the reservoirs. The method should also be environmentally benign, and be economical in use. The method should also provide a means for branding the injected $CO_2$ so as to identify the source/ownership of the sequestered $CO_2$.

SUMMARY OF INVENTION

An object of the present invention is to provide a method for detecting leaks from geological formations used to store $CO_2$ that overcomes many of the disadvantages of the prior art.

Another object of the present invention is to provide a method to monitor the leakage of carbon dioxide from geological reservoirs. A feature of the invention is the use of tracers whereby the tracers are pumped into the reservoirs along with the carbon dioxide. An advantage of this feature is that levels of the tracers are unaffected by atmospheric gases due to the tracers' low background levels in the atmosphere.

Still another object of the present invention is to provide a highly sensitive method to monitor the leakage of carbon dioxide from geological reservoirs. A feature of the invention is the use of perfluorocarbons (PFTs) as tracers. An advantage of this feature is that PFTs are detectable at extremely low concentrations, as low as approximately $10^{-16}$ mol/L.

Yet another object of the present invention is to provide a method for leak detection of $CO_2$ from geologic repositories wherein the materials used are of low cost. A feature of the invention is the low detection limits of the tracers used by the instant invention. An advantage of the invention is that very minute quantities of the tracers are used for carbon dioxide leak detection, thus aiding in lower operational costs.

Still another object of the present invention is to provide a method that provides alternative gases for leak detection of $CO_2$ from geologic formations. A feature of the invention is the use of methane, ethane, and propane gases as early indicators or detectors of carbon dioxide leakage and the rate of leakage. These gases are displaced by the carbon dioxide gas and therefore serve as a means of forecasting $CO_2$ leakage before actual leakage of $CO_2$ from the reservoir occurs. An advantage is that methane, ethane, and propane gases are naturally present in the sequestration reservoir and areas above it, and therefore, utilization of these tracers incurs no material costs.

Yet another object of the invention is to provide a method for sampling for the presence of and to determine the concentrations and isotopic make-up of endemic soil gases before and after underground $CO_2$ injection of carbon dioxide leak detection from geological sequestration reservoirs based upon determination of the carbon dioxide concentration in endemic soil gas and the carbon dioxide flux in endemic soil gases. A feature of the invention is the use of gas flux (volumetric flow) or gas accumulation chambers placed on the ground in the zone to be monitored. An advantage of this feature is that the gas accumulation chambers primarily collect gases emanating from the soil and deep earth which are not confounded by the high atmospheric background of carbon dioxide.

Still another object of this invention is to provide a method for the measurement of methane, ethane, propane, and radon concentration and flux in soil gases in regions above anticipated $CO_2$ plume locations, the plume caused by $CO_2$ injection in those locations. Measurements of the endemic gases are taken before and after sequestration. A feature of this invention is that migration of endemic gases to the surface is facilitated by an upward flow of carbon dioxide which acts as a carrier gas. An advantage of this feature is that the increase in endemic gas flux to the surface can be an indicator of $CO_2$ leakage to the surface.

Yet another object of this invention is to provide a method of establishing ownership of carbon dioxide stored in geologic reservoirs. A feature of this invention is the assignment to each injector, and carbon dioxide owner a unique set of tracers that are added to their carbon dioxide. An advantage of this feature is that the sequestered carbon dioxide is labeled with its owner's brand or identification.

Another object of the invention is to provide a method to monitor the atmosphere directly above the sequestration site.

Yet another object of the invention is to provide a method to monitor the sequestration site using shallow water wells.

Briefly, the invention provides a device for use in the measurement of soil gases, the device comprising an enclosure; gas-specific absorbent contained within said enclosure; a means for facilitating fluid communication of the gas to the absorbent; and a means for preventing ground water from entering the enclosure.

The invention also provides a method for the measurement of carbon dioxide leakage from sequestration reservoirs, the method comprising adding tracer molecules to carbon dioxide; allowing the tracer molecules and carbon dioxide to mix homogeneously; injecting the homogeneous mixture of tracer molecules and carbon dioxide into sequestration reservoirs; and collecting leaked tracer molecules at and near the external surfaces of the reservoirs.

In addition, the invention provides a process for forecasting carbon dioxide leakage from sequestration reservoirs, the method comprising measuring first endemic gas concentrations at the sequestration reservoir; injecting carbon dioxide into the reservoirs; measuring second endemic gas concentrations after the injection of carbon dioxide; and taking the difference of the first and second concentrations.

Further, the invention provides a method for branding sequestered carbon dioxide, the method comprising injecting a predetermined mixture of perfluorocarbons into each reservoir of sequestered carbon dioxide, the predetermined mixture indicative of the anthropogenic source of carbon dioxide.

BRIEF DESCRIPTION OF DRAWING

For the purpose of illustrating the invention, the drawing shows a form of the invention which is presently preferred; it being understood, however, that the invention is not limited to the precise arrangement and instrumentality shown, wherein.

DETAILED DESCRIPTION OF THE INVENTION

The instant invention provides methods for the verification of barrier integrity. In particular, this invention provides a method for the detection of carbon dioxide gas leakage from sequestration reservoirs. The method provides for a more sensitive leak analysis inasmuch as sulfur- and/or halogen-containing tracer moieties are used. The invention also provides a process for the sampling and measurement of methane and carbon dioxide in soil gases to differentiate between unsequestered (i.e., ubiquitous) carbon dioxide coming from in or near the surface and any leaking carbon dioxide which has been injected.

Aside from atmospheric sources of methane and carbon dioxide, methanogenic bacteria in the soil adds to the ubiquitous methane load. This methane can be distinguished from deep geologically stored methane. The isotopic distribution of methane from bacteria is different from the isotopic distribution of methane from deep geological sources for reasons very similar to those for the two types of carbon dioxide discussed supra. Methane naturally found in the deep earth is distinguishable from methane produced by methanogenic bacteria in the soil by measuring the isotopic distribution of carbon ($^{12}C$ and $^{13}C$) in both sets of methane. This methane concentration and flux from methanogens can vary seasonally and have a different carbon isotopic distribution than methane displaced from deep geologic formations which migrates to the surface.

Carbon-13 ($^{13}C$) to carbon-12 ($^{12}C$) ratios are compared to differentiate between carbon dioxide emanating from biological sources and the sequestered carbon dioxide.

In addition, the invention provides a process for the verification of barrier integrity for $CO_2$ sequestration by monitoring the concentrations of methane, ethane, and propane in soil gas, and separately radon, from the sequestration reservoirs.

Increases in the concentration of methane, ethane, propane and hydrocarbons characteristic of the reservoir from the deep earth in soil gas and increases in their flux are prospective indicators of possible leakage of carbon dioxide from the sequestration reservoir. These gases are proxy gases whose increased presence at the surface are indicative of imminent carbon dioxide leakage from the storage reservoir.

The primary significance of hydrocarbons such as methane, ethane, propane and hydrocarbons characteristic of the reservoir is as an early indicator of a potential pathway for $CO_2$ leakage to follow. Hydrocarbons are displaced by moving carbon dioxide and would be pushed out ahead of $CO_2$ during injection. Radon is carried with the leaking carbon dioxide, and its increased concentration and flux in soil gas after carbon dioxide injection is a concurrent indicator of carbon dioxide leakage.

Background measurements of carbon dioxide, methane, ethane ($C_2H_6$), propane ($C_3H_8$), other hydrocarbons characteristic of the reservoir, and radon are carried out before the sequestration of carbon dioxide in a potential sequestration reservoir. The isotopic distribution of elemental carbon in the carbon dioxide and methane are determined. The amount of carbon dioxide in soil gas that is present as a result of degradation of plant matter and other natural processes is measured seasonally before carbon dioxide injection. This carbon dioxide which results from natural processes has a different carbon isotopic distribution than carbon dioxide being injected into the formation due to different proportions of carbon-12 ($^{12}C$) and carbon-13 ($^{13}C$).

The concentration, flux and isotopic distribution of carbon dioxide is again measured seasonally after sequestration begins. The values are corrected for the amount of carbon dioxide arising from natural processes, giving the amount due to leakage. If one uses a commercially available instrument to measure the carbon dioxide soil gas flux, the instrument must be modified by adding a gas sampling port to the analysis chamber that allows periodic withdrawal of gas samples, for the determination of the carbon isotope ratios in $CO_2$ and $CH_4$.

The previously determined baseline measurements are subtracted from the measurements made after carbon dioxide is sequestered in the reservoir. Radon concentration levels can be measured through alpha-particle counting.

Figure 1:
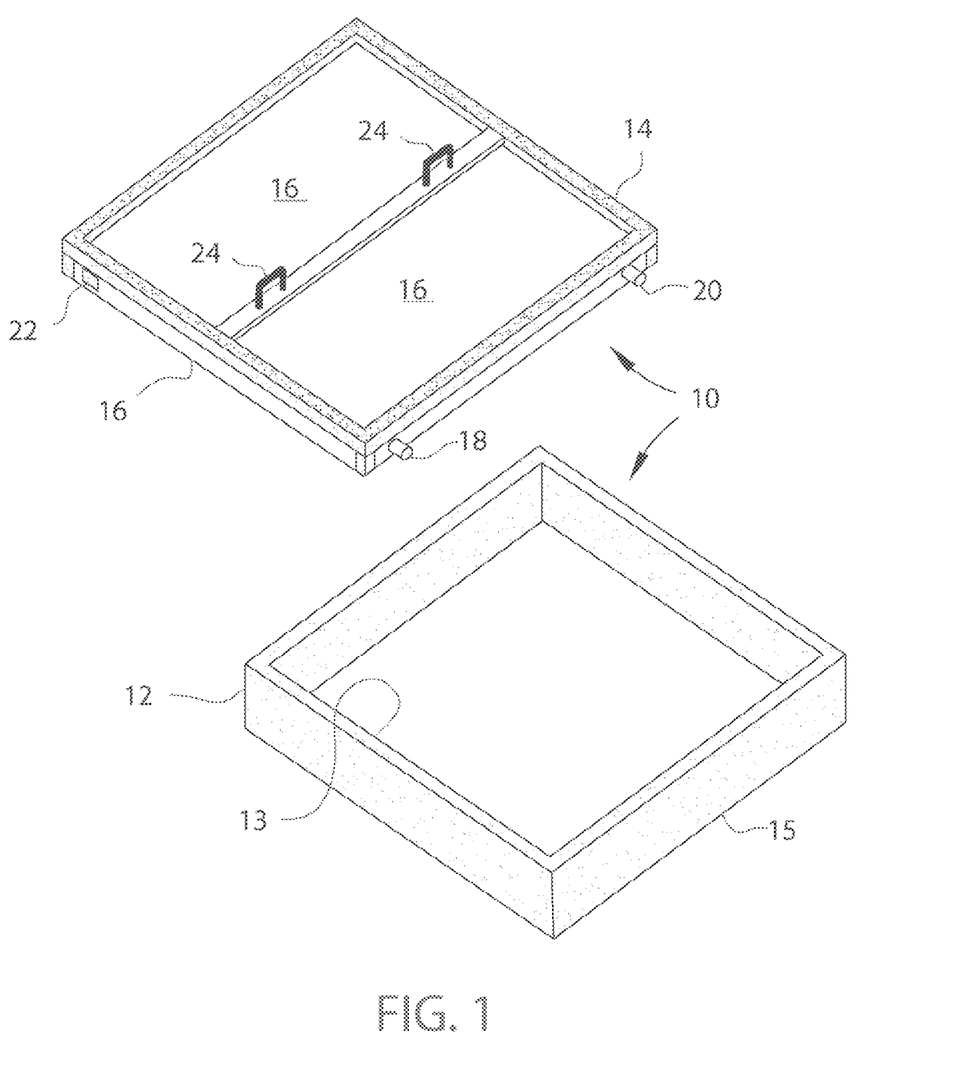
FIG. 1 depicts a gas accumulation chamber, in accordance with features of the present invention.

The concentration of ethane and propane and higher hydrocarbons characteristic of the reservoir in soil gas and their flux rate can be measured by sampling and analysis of gases from a conventional gas collection box, FIG. 1 infra. Alternately, the concentration of these gases and higher hydrocarbons in soil and their flux can be measured using adsorbent packets and analytical technology available from W. L. Gore Corp., Exploration and Research Division, Elkton, Md. The Gore packets are desorbed and the resulting gases analyzed by conventional gas chromatography or combined gas chromatography-mass spectrometry.

In the alternative, carbon dioxide flux can also be measured using a carbon dioxide soil gas flux device. See FIG. 2 infra. The carbon isotopic distribution of the carbon dioxide withdrawn from the gas analysis chamber of the soil gas flux device is then determined using isotope ratio mass spectrometry or a similar technique.

As with the carbon dioxide measurements, the amount of methane in soil gas and its isotopic distribution that is present as a result of methanogenic bacteria is measured seasonally before carbon dioxide injection. The concentration, flux, and isotopic distribution of methane are also measured seasonally after sequestration begins. The concentration and flux values are corrected for the amount of methane and flux arising from natural bacterial processes, giving the amount due to displacement resulting from carbon dioxide leakage. Natural processes do not typically form ethane and propane. Any increase in the concentrations and fluxes of ethane and propane after sequestration relative to the amounts of ethane and propane before sequestration is a result of displacement from deep geological formations.

Tracer Detail

Tracers can be added to the carbon dioxide in a sequestration reservoir in a number of ways. One way is to add a known amount of tracer to a known amount of carbon dioxide. Preferably, addition of the tracer is done over the entire course of injection of the known amount of carbon dioxide into the reservoir. Two or more tracers can be added simultaneously or at different times to the carbon dioxide. The use of multiple tracers at a single site can aid in the improvement of the spatial resolution of the breach or leak zone. The tracers can be used at any carbon dioxide injection pressure high enough to cause the carbon dioxide to permeate through the host rock in the sequestration reservoir inasmuch as carbon dioxide permeation, acting as a carrier force, causes the tracers to also migrate and permeate through rock.

Suitable tracer molecules include, but are not limited to, carbon tetrafluoride ($CF_4$), hexafluoroethane ($C_2F_6$), ethane ($C_2H_6$), sulfur hexafluoride ($SF_6$), carbon-13 labeled carbon dioxide ($^{13}CO_2$), carbon disulfide ($CS_2$) and molecules containing perfluoro functional groups.

The use of multiple PFT tracers at a single barrier site can serve to improve the spatial resolution of the barrier breach(s). PFTs are perfluorinated alkyl-substituted cycloalkanes which are nontoxic, inert, chemically stable up to 500° C., and uniquely detectable at extremely low levels, down to approximately $10^{-16}$ mol of PFT per liter (mol/L) or to femtogram ($10^{-15}$ gram) quantities of the PFTs. These levels of detection are less than part-per-trillion (ppt) concentrations.

PFTs have sufficiently low boiling point temperatures (40° C. to 120° C.) and, accordingly, sufficiently high vapor pressures for their use as tracers. These properties of PFTs allow these compounds to readily diffuse upwards when they escape from the sequestration host formation. Organofluorocarbons have enhanced solubility in carbon dioxide relative to their hydrocarbon analogues (such as dimethylcyclobutane and methylcyclopentane), and also have very low water solubility. Thus, the PFTs will stay with gaseous and/or liquid carbon dioxide rather than partition substantially into petroleum, coal and/or water.

Exemplary PFTs include the perfluoro mono and polymethyl cylcopropanes, the perfluoro mono and polymethyl cylcobutanes, the perfluoro mono and polymethyl cyclopentanes and the perfluoro mono and polymethyl cylcohexanes. Exemplary, specific perfluoro compounds include, but are not limited to, perfluoromethylcyclopropane ($C_4F_8$), perfluorodimethylcyclopropane ($C_5F_{10}$), perfluoro-trimethylcyclopropane ($C_6F_{12}$), perfluorotetramethylcyclopropane ($C_7F_{14}$), perfluoropen-tamethylcyclopropane ($C_8F_{16}$), perfluorohexamethylcyclopropane ($C_9F_{18}$); perfluoro-methylcyclobutane ($C_5F_{10}$), perfluorodimethylcyclobutane (PDCB/$C_6F_{12}$), perfluorotri-methylcyclobutane ($C_7F_{14}$), perfluorotetramethylcyclobutane ($C_8F_{16}$) perfluoropenta-methylcyclobutane ($C_9F_{18}$), perfluorohexamethylcyclobutane ($C_{10}F_{20}$), perfluoro-heptamethylcyclobutane ($C_4F_8$), and perfluorooctamethylcyclobutane ($C_{12}F_{24}$); perfluoromethylcyclopentane (PMCP/$C_6F_{12}$), perfluorodimethylcyclo-pentane ($C_4F_8$), perfluorotrimethylcyclopentane $C_8F_{16}$), perfluorotetrameth-ylcyclopen-tane ($C_9F_{18}$), perfluoropentamethylcyclopentane ($C_{10}F_{20}$), perfluorohexamethylcyclo-pentane ($C_{11}F_{22}$), perfluoroheptamethylcyclopentane ($C_{12}F_{24}$), perfluorooctamethyl-cyclopentane ($C_{13}F_{26}$), perfluorononamethylcyclopentane ($C_{14}F_{28}$), perfluorodeca-methylcyclopentane ($C_{15}F_{30}$); perfluoromethylcyclohexane (PMCH/$C_7F_{14}$), perfluorodimethylcyclohexane (o-PDCH and m-PDCH and p-PDCH/$C_8F_{16}$), perfluorotrimethylcyclohexane (PTCH/$C_9F_{18}$), perfluorotetramethylcyclohexane ($C_{10}F_{20}$), perfluoropentamethylcyclohexane ($C_{11}F_{22}$), perfluorohexamethylcyclohexane ($C_{12}F_{24}$), perfluoroheptamethylcyclohexane ($C_{13}F_{26}$), perfluorooctamethylcyclohexane ($C_{14}F_{28}$), perfluorononamethylcyclohexane ($C_{15}F_{30}$), perfluorodeca-methylcyclohexane ($C_{16}F_{32}$), perfluoroundecamethylcyclohexane ($C_{17}F_{34}$), perfluorododecamethylcyclohexane ($C_{18}F_{36}$).

This List of Cyclic Perfluorocarbons Includes any and all Geometric and positional substitution isomers. It also includes the analogous set of perfluoroethyl compounds, and perfluoro-n-propyl compounds and perfluoroisopropyl compounds.

Tracer Monitoring Detail

To investigate diffusion or transport of $CO_2$ out of the reservoir, tracer monitoring sites are established near the point of injection, at fracture zones, and at formation outcroppings, as well as any area or volume above or around the underground $CO_2$ plume, including atmospheric monitoring and shallow aquifer monitoring.

Both active and passive tracer monitoring with penetrometers (See FIG. 4) are used to detect leakage and to determine leakage rates. Both types of tracer monitoring are carried out with the aid of carbonaceous sorbents. A myriad of suitable sorbents are commercially available, including CATS (Capillary Adsorbent Tracer Samplers) from Brookhaven National Laboratory, Upton, N.Y. The exposed sorbents are analyzed by thermal desorption with subsequent gas chromatographic analysis to determine the level of tracer leakage at the reservoir test sites.

Figure 4:
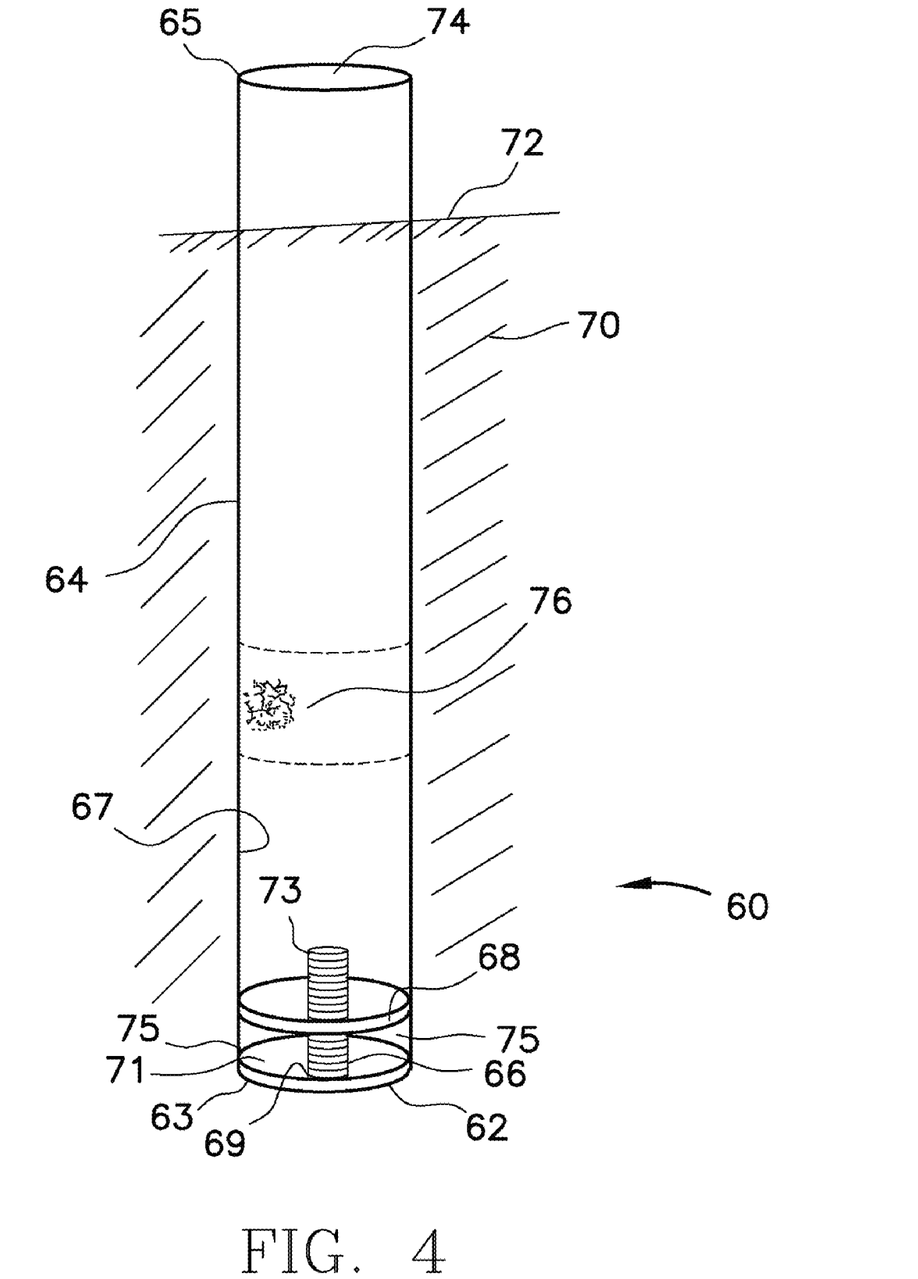
FIG. 4 is an elevational, partial cut-away view of a detachable head penetrometer, in accordance with features of the present invention.

Active monitoring utilizes a pump to continuously remove soil gases from the penetrometer, FIG. 4, pass the soil gases through a sorbent tube for subsequent analysis, then return the gases to the penetrometer. This contrasts with passive monitoring which allows the soil gases to naturally diffuse through the chamber defined by the penetrometer's casing, FIG. 4 then into the sorbents tube. The advantage of active monitoring is a larger soil-gas sample and thus, enhanced leak detection sensitivity.

Baseline atmospheric blanks are taken using CATS sorbents at various locations in a passive (non-pumped) mode for an empirically determined period of time suitable for adequate adsorption (e.g., two minutes) of target tracers, during which time CATS sorbents are being placed in monitoring holes. This mode or manner mimics the necessary atmospheric manner and time the CATS sorbents used underground in the penetrometers would receive for actual leak monitoring, while being placed into and removed from monitoring holes. The atmospheric tracer background is also measured prior to the injection of carbon dioxide into sequestration reservoirs by using a sampler such as CATS and a hand pump.

Background methane and radon are measured. First, the mixture of $O_2$ and tracer are injected into the target geologic formation. The faster the tracer appears at the surface, the greater the average linear velocity of the leaking carbon dioxide/tracer toward the surface. Average linear velocity is related to the flow rate of the leaking gas. Lower flow rates are associated with the presence of less permeable cap rocks. The fewer fractures and microfractures in the cap rock, the longer it will take for carbon dioxide and/or tracer to appear at the surface.

The aforementioned tracers can be used in the manner described for the purpose of branding sequestered carbon dioxide as a means of ownership identification. The method comprises injecting a predetermined and registered (for ownership identification purposes) mixture of perfluorocarbons and/or other chemical tracers into sequestered carbon dioxide.

Monitoring Using Carbon Dioxide Soil Flux Detail

The concentration of carbon dioxide in soil gas and the carbon dioxide flux in soil gas at and near the sequestration site is determined for four seasons of the year before and after sequestration begins. Each season of the year before injection of carbon dioxide begins, measurements are made of soil gases. Seasonal variations are important. Carbon dioxide fluxes or volumetric flow rates are generally higher in warmer, wetter seasons than in cooler, drier seasons. Warm and wet seasons most likely allow higher carbon dioxide fluxes into the atmosphere, and higher soil carbon dioxide than colder, dryer weather.

The carbon isotopic ratio in the carbon dioxide sampled from the soil gas is measured in samples taken before and after sequestration begins. Soil gas samples are collected using a gas accumulation chamber designated in FIG. 1 as numeral 10. The box comprises a plurality of substrates arranged to form a square, rectangle, triangle, circle, or other suitable closed loop configuration to serve as a base 12. A frame 14 is adapted to be received by an upwardly facing edge 13 of the base 12. Transparent panels 16 are contained within the boarders of the frame so as to provide visual communication with the inside of the box. A downwardly facing edge 15 of the base is adapted to be forced into the soil so that when the base is so situated on a sampling site, and the frame 14 atop the base, the frame-base combination defines an interior space for gas accumulation and isolation from the atmosphere.

A gas outlet 18 (to a $CO_2$ analyzer, not shown) and a gas inlet 20 (from the $CO_2$ analyzer) are formed in regions of the frame and separated by a distance suitable to prevent fluid interference between the two ports during gas ingress and egress. Another region of the frame defines a sampling port 22 having a rubber septum. Upwardly extending handles 24 serve to lift the frame 14 off the base and are situated along a medial line of the frame 14.

A preferred embodiment of the chamber measures 1 meter (m) (length) by 1 m (width) by 20 centimeters (cm) (depth). The soil gas accumulation chambers can be any container of any size. The larger the container, the more representative a sample of soil gas the chamber collects.

Figure 2:
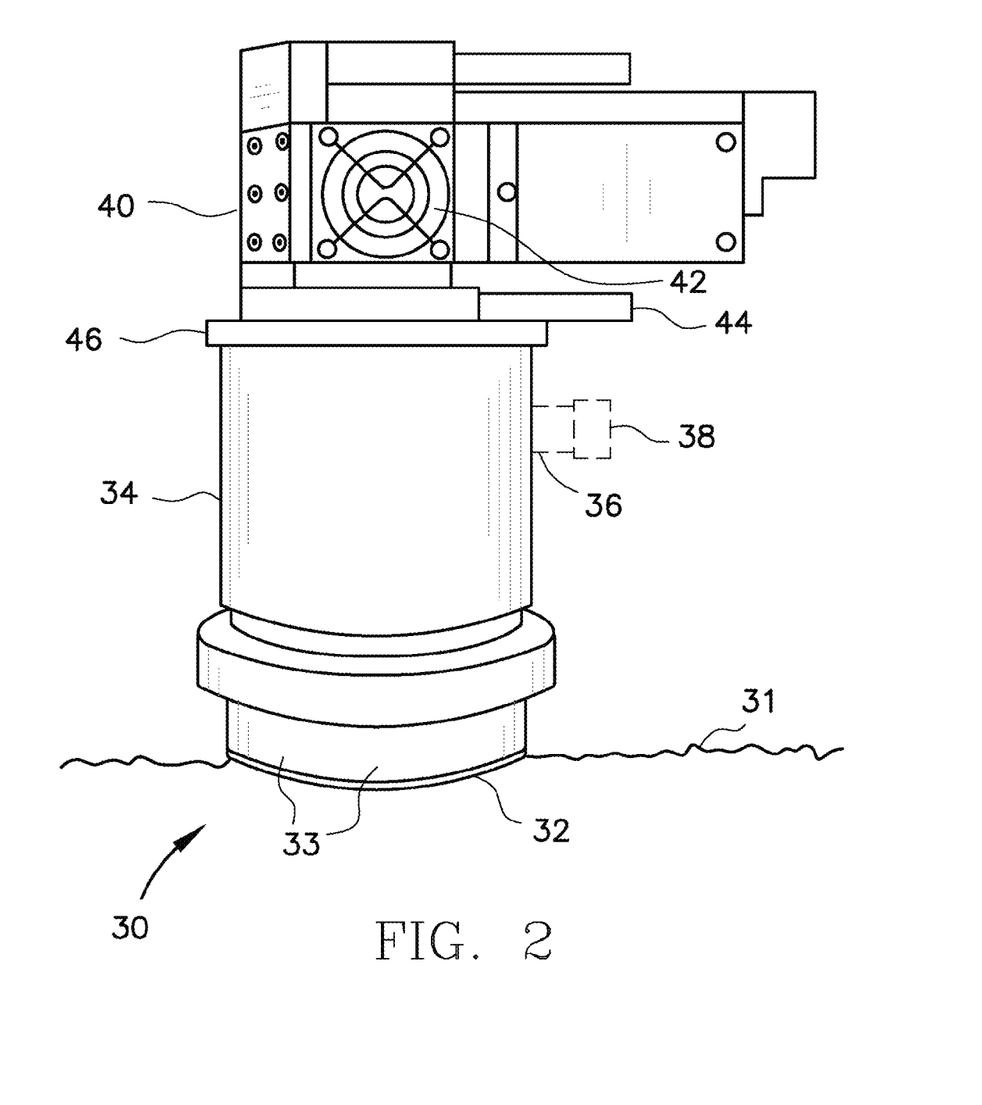
FIG. 2 depicts a modified Li-Cor instrument for use in the measurement of $CO_2$ flux from soil gases, in accordance with features of the present invention.

In the alternative, a commercially available carbon dioxide soil gas flux monitor such as a Li-Cor Biosciences Model 6400-09 (Lincoln, Nebr.), which has been modified and is designated in FIG. 2 as number 30, can be used to determine the carbon dioxide flux in soil gas. The monitor 30 is partially embedded into the ground via a depending knife edge collar 32, which is positioned along a peripheral edge of a downwardly facing surface of the monitor 30. Carbon dioxide emanating from the sample surface 31 enters a collection cavity 34 via a plurality of gas means of ingress 33. A sample of the carbon dioxide can be obtained for carbon isotope or other analyses from the Li-Cor monitor's gas accumulation chamber 34 via an added gas sampling port 36 fitted with a septum 38. The monitor has a detachable infrared (IR) gas analyzer sensor head 40. The IR analyzer sensor head 40 includes a cooling fan 42 and tubing 44 which attaches to a carbon dioxide scrubber (not shown). The IR analyzer sensor head 40 attaches to an analyzer mounting plate 46. The Li-Cor monitor can also be used for the collection of samples for analysis of the fluxes of methane, ethane, and propane.

A continuous carbon dioxide analyzer is used to measure the carbon dioxide concentration in the gas accumulation chamber. The carbon isotopic distribution in the carbon dioxide in the box is determined by taking a gas sample from the box after a predetermined period of collection time. Fluid communication between the outside and inside regions of the chamber is facilitated with a syringe accessing the inside regions via a septum transversely arranged through a substrate wall forming a portion of the base of the box. Gas samples are taken from the gas accumulation chamber and the carbon isotopic distribution in the carbon dioxide is measured using isotope ratio mass spectrometry.

The gas accumulation chamber of the modified Li-Cor instrument has a collar that is simply pressed into the ground. The aforementioned substrates comprising the base 12 of the collection box further define rigid material able to withstand the pressure necessary to force downwardly facing edges of the substrates into soil surfaces. Preferably, the downwardly facing edges 15 of the base defines a metal knife-like substrate (i.e., a depending edge of the collar) attached thereto so as to provide a nearly air tight seal to the ground at least so as to prevent free exchange of gases with the atmosphere. The seal can be broken and reset to move the box or the gas accumulation chamber to other locations.

Figure 3:
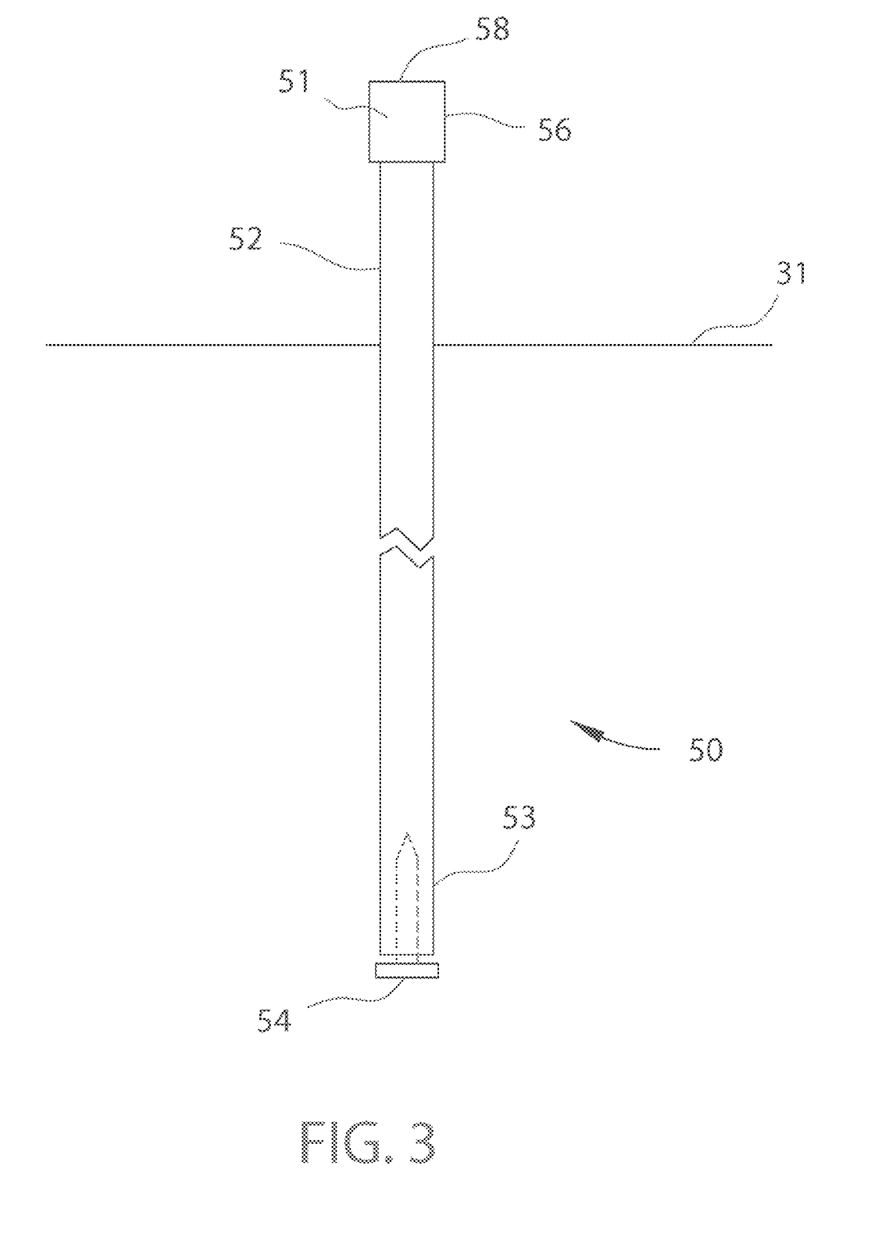
FIG. 3 depicts a soil probe used to sample soil gases for carbon isotope measurements, in accordance with features of the present invention.

In yet another alternative, samples of carbon dioxide, methane, and other gases from soil gas for carbon isotope ratio measurements and/or other analyses can be obtained using a small soil probe as depicted in FIG. 3 as numeral 50. The probe is defined by a tube 52 having a first end 51 and a second end 53. A solid, elongated and taper substrate, such as a nail 54 fits loosely into an open end of the tube 52. The nail 54 has a head sufficiently large to cover the opening in order to keep the end from being clogged with soil when the second end is positioned below the soil surface "S". The first end 51 of the tube 52 is adapted to receive a cap 56 fitted with a septum 58.

The probe 50 is pushed or otherwise inserted into the ground up to 1 meter along its longitudinal axis so as to be in a position to receive soil gas samples. Samples residing within the interior of the tube can be removed by puncturing the septum with a syringe.

Penetrometer Detail

Penetrometers are commercially available devices used to determine soil compaction. A modified penetrometer serves as a means of tracer(s) collection from soil gases in the instant invention.

Generally, and as depicted as number 60 in FIG. 4, a penetrometer is defined by an elongated tubular body 64 having a first end 63, and a second end 65. An end plate 62 is in slidable communication with the first end 63 of the penetrometer so as to be in frictional engagement with an inside longitudinally-extending surface 67 of the tubular body 64. One configuration to facilitate this slidable communication is depicted in FIG. 4 as comprising a coaxially aligned threaded aperture plate 66 situated inwardly from the end plate 62 (i.e. medially along the longitudinal axis α of the tubular body) whereby the aperture plate 68 is rigidly attached to the end plate 62. A threaded rod 68 serves as a means for rigidly attaching the aperture plate 66 to the end plate 62 whereby the proximal end 69 of the rod 68 is attached to a medially facing surface 61 of the end plate 62 and the distal end 73 of the rod 68 is threadably received by a threaded aperture defined by the aperture plate 66. As with the end plate 62, the aperture plate 66 also is in slidable communication with the inside surface 67 of the tubular member 64.

Situated medially from the inside surface of the penetrometer tubular body 67 is a sorbent tube such as a CATS. Suitable dimensions of the tube include a ¼ inch outer diameter (o.d), 3/16 inch inner diameter (i.d.) glass tubing that is about 2-in long containing 60 mg of activated carbon, such as Ambersorb™, Rohm and Haas, Philadelphia, Pa. Generally, the activated carbon resides within the tube. The sorbent tube is open at one end and is equipped with a plug of inert, permeable material at each end to keep the activated carbon in place. The sorbent tube is suspended or removably attached to a region of the inside surface 67 of the tubular body 64 via a hanging basket, string, or some other removably positioning means.

In operation, the first end 63 of the penetrometer is driven into the soil 70 so that most of the penetrometer 60 is beneath the soil surface 62. An elongated substrate such as a metal rod (not shown) is inserted through the open top end 74 of the tube 64. The elongated substrate is used to pound the threaded aperture plate 66 with sufficient force to cause the end plate 62 to protrude out of the tube 64 and a few inches down into the soil 70. Tack welds 75 (or other means to prevent axial movement beyond a certain point) prevent the threaded aperture plate 66 from also exiting the tube 64. Those welds 75 are situated between the end plate 62 and aperture plate 66 and circumferentially along the inside surface 67 of the tube 64.

A CATS sorbent packet 76 is positioned just above the bottom of the tube 64, a few inches above the soil surface (not shown) within the tube 64 by a string or some other means (not shown). This exposes the absorbent 76 within the sorbent tube to soil gases via upward diffusion of the soil gases and protects the absorbent 76 from ground water. To allow free exchange of soil gas with the absorbent, the aperture plate 66 defines a plurality of apertures to facilitate vapor passage therethrough.

The second end 65 of the tube 64 is then hermetically sealed, e.g., with a rubber stopper (seal not shown). The seal serves as a means to prevent contamination of the sorbent packet from ambient tracers and also serves as a means to prevent water from entering the penetrometer from the soil. Specifically, the imposition of the seal prevents tracers that may have formed an aerial plume from affecting the sorbent packet's absorbent 76. Also, with the presence of the seal, the entry of water into the first end 63 of the penetrometer would create a positive pressure within the tube 64. The requirement of a positive pressure against the ambient barometric pressure of the surroundings, such as the soil 70, prevents the entry of water.

Early Leak Detection Using Proxy Gases Detail

As noted supra, the concentration and flux of methane, ethane, propane, and hydrocarbons characteristic of the reservoir and radon in soil gas are measured before and after sequestration. The concentration and flux of methane, ethane, and propane in soil gas are determined by gas chromatography by sampling gases from the one meter square gas accumulation chamber, FIG. 1 supra, the accumulation chamber of a modified Li-Cor model 6400-09 instrument, FIG. 2 supra, the soil probe, FIG. 3 supra, or a similar instrument. Hydrocarbons in soil gas can also be sampled using the sorbent packets situated within a penetrometer, FIG. 4, using the Gore soil gas sampling and analysis system.

Alternately, the concentration of $CH_4$, $C_2H_6$, and $C_3H_2$ in the atmosphere above the sequestration formation can be determined remotely using an aircraft mounted Differential Absorption Lider (DIAL) system such as that developed by Kodak [D. Brake, M. Clayton, S. Stearns. "Advanced Airbourne Natural Gas Leak Detection System Overview,"] and presented at the Second National Gas Technologies Conference and Exhibition, Phoenix, Ariz., Feb. 9-11, 2004.

The surface flux of carbon dioxide, methane, ethane, and propane is measured 1 square meter ($m^2$) for every 2500 $m^2$ of surface, or more frequently per each 2500 $m^2$. (The more surface sampling points one acquires soil gas samples from using the gas collection boxes, the more reliable the resulting data.) One preferred embodiment of the gas surface flux determination is the measurement of 1 $m^2$ per every 2500 $m^2$ of surface.

Surveys of light- and heavy-hydrocarbons which are known to be characteristic of underground reservoirs can be made using shallow (2 foot) soil monitoring holes containing Gore-Sorber sampling modules, available from W.L. Gore Corp. noted supra. These modules contain collection of adsorbent materials that are effective in collecting abroad range of volatile organic compounds. These adsorbent packets are later desorbed and the resulting gases analyzed by conventional gas chromatography or gas chromatography-mass spectrometry.

Radon Measurement Detail

Radon measurements are performed by taking advantage of the fact that radon is the only gas that emits alpha particles. A gas sample is drawn into a sample cell that is coated with zinc sulfide. When an alpha particle collides with zinc sulfide, a photon is emitted which can be detected by a photo multiplier and counted. An example is the Pylori Electronics (Ottawa, Canada) Model AB-5 Detection System used with the Model 300A Scintillation Chamber. Two isotopes of radon are commonly detected. Rn-222 (referred to commonly as "radon") has a radiative half-life of 3.82 days, and Rn-220 (known commonly as "thoron") has a half-life of 54.7 seconds. The two isotopes can be measured simultaneously in a gas sample and differentiated by the distinctly different decay rates.

Radon measurements are performed both before and after sequestration of carbon dioxide. Any increased flux of Rn gas upon the commencement of carbon dioxide sequestration can serve as a concurrent indicator (along with increased fluxes of carbon dioxide, methane, ethane, and propane) of carbon dioxide leakage.

Carbon Dioxide Isotopic Analysis

The overall sequestration reservoir leak rate can be calculated using either/or both the tracer measurements and the measured increase in $CO_2$ surface flux rate in endemic soil gases. The surface flux rate after $CO_2$ sequestration is compared to the $CO_2$ flux rate measured before sequestration. Any increased amount of $CO_2$ is due to carbon dioxide leaking from the sequestration reservoir. Any increased flux of methane, ethane, propane, and/or radon serve as a forecast of $CO_2$ leakage from the reservoir.

The isotopic distribution of the leaked carbon dioxide is compared with the known isotopic signature of the $CO_2$ pumped into the reservoir, and with the isotopic distribution of $CO_2$ derived from biological activity. The ratio of stable carbon isotopes in $CO_2$ can provide important information as to the its source. In general the ratio is expressed as compared to an established standard (Pee Dee Belemnite, a carbonate mineral) according to Equation 1.

$$\delta^{13}C = \frac{(^{13}C/^{12}C)_{sample} - (^{13}C/^{12}C)_{standard}}{(^{13}C/^{12}C)_{standard}} \times 1000 \quad \text{Equation 1}$$

where the units are expressed in permil (decimal fraction multiplied by 1000) (or ‰). Carbon is designated by its chemical symbol "C" in equation 1. In general, biological sources produce isotopically "light" $CO_2$ with $\delta^{13}C$ being strongly negative, while geologic sources lead to less negative values. By measuring the $\delta^{13}C$ for soil gas $CO_2$ as well as the injected $CO_2$, it is possible to identify the source of $CO_2$ leaking to the atmosphere.

As noted supra, a salient feature of the invention is the use of gases other than carbon dioxide such as methane, ethane, propane, and radon for verification of barrier integrity. In addition, sulfur and/or halogen-containing molecules are used as tracers for verification of barrier integrity, in particular for $CO_2$ leak detection.

A preferred embodiment for the tracers is perfluorocarbons (PFTs).

The operation detail described infra is for illustrative purposes and is not meant to exclude other modes of operation.

Operation Detail

Figure 5:
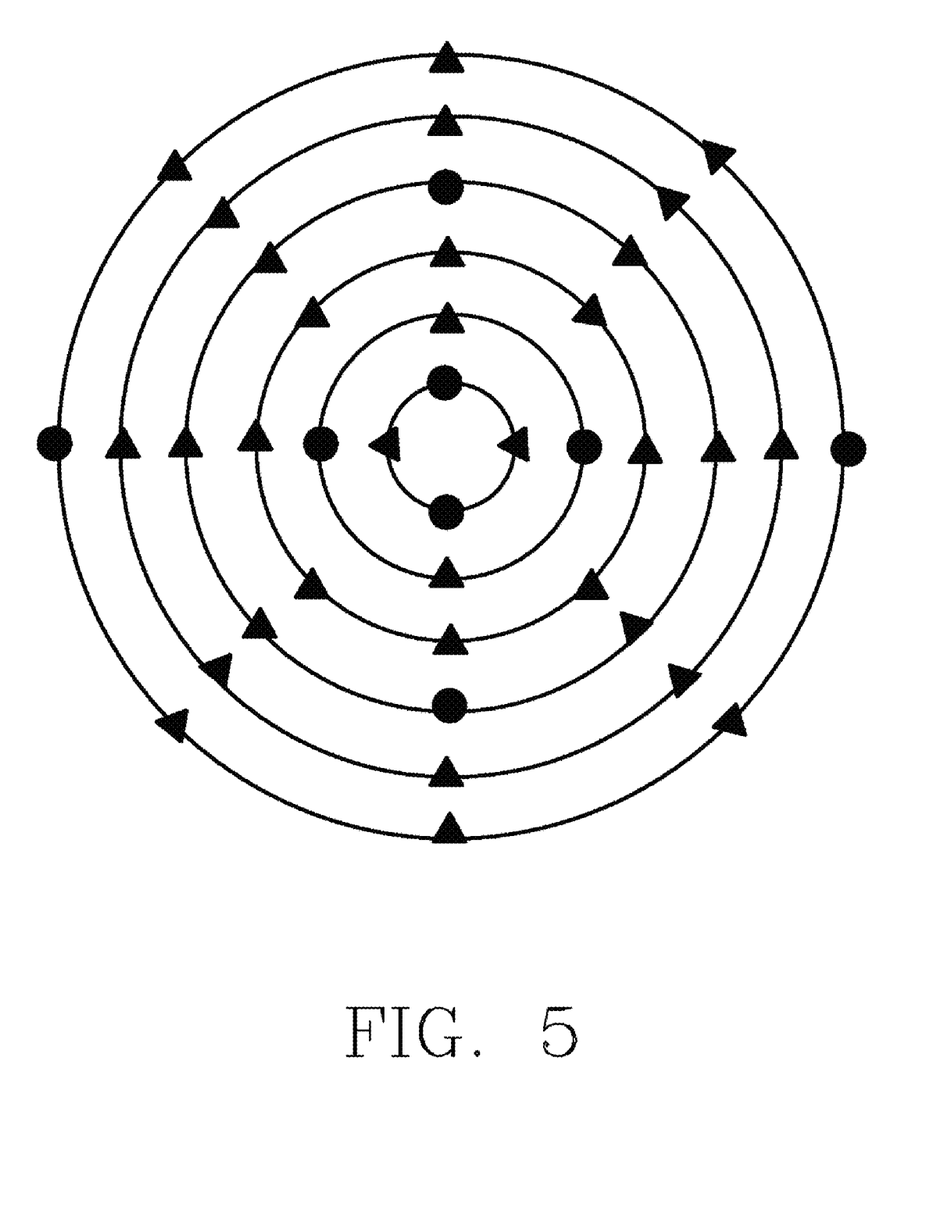
FIG. 5 is a schematic diagram which depicts a matrix of passive and/or active monitoring sites placed in a series of concentric circles with a diameter of several hundred meters around a carbon dioxide injection well, in accordance with features of the present invention.

A matrix of passive and/or active monitoring sites (typically 40 or more such sites) is placed in a series of concentric circles with a diameter of several hundred meters around a carbon dioxide injection well. This concentric placement is depicted in FIG. 5. The circles in FIG. 5 represent active monitors where pumps are used to pull gases out for measurement and the solid triangles represent passive monitors such as CATS absorbents and penetrometers 60, FIG. 4. The injection well would be at the center of the circles in FIG. 5.

The ratio of active monitoring sites to passive sites is determined by the topography of the surface area over the sequestration reservoir. A typical ratio of passive sites to active sites is 10:1. Passive sites are favored because they require less maintenance and are less manpower-intensive. A higher proportion of passive sites exists in a situation where there are restrictions on the number of active sites, e.g., in very forested or rugged areas where solar cell power or other power sources are not feasible.

Carbon dioxide mixed with one or more tracers is injected into the reservoir. The carbon dioxide is injected as a liquid or gas at a well head. At sequestration reservoir depth in most host geologic formations, the carbon dioxide is well above its critical point, i.e., pressure more than 73 atmospheres and temperature above 31° C., and thus is a gas. (The critical point of carbon dioxide is 31° C. and 73 atmospheres, i.e., the combination of temperature and pressure above which carbon dioxide can not be liquified.)

Sampling methodology using absorbents comprises constructing a grid of 40 or more holes in the surface which are to be monitored. Sampling holes are placed at or near potential sources of leakage such as wells, including the injection well (for $CO_2$), fault zones, and other features with areas of depression near the surface. Monitoring holes are also placed near these areas where sampling and analysis of proxy gases such as methane, ethane, propane, and radon has indicated an increased presence in the soil gas and an increased flux of these gases.

Tracer soil gas monitoring holes are made by driving ¾ inch steel pipe penetrometers 60, supra, into the ground to a depth of several feet. The CATS sorbents contained within the penetrometer are subsequently exposed to soil gas for intervals from about one week to two months before being retrieved and sent to a laboratory for analysis. Prior to placing a sorbent into a tube, PFT is added in a known constant proportion to the carbon dioxide as it is injected into a geologic formation for sequestration.

The methods herein can be applied to any geologic formation being used for carbon dioxide sequestration including, but not limited to, active and depleted oil and gas fields, natural gas hydrates, coal beds, brine aquifers, shale formations, and salt domes.

Leak Monitoring Example

Approximately 2,100 tons of carbon dioxide were injected into a depleted oil well. Three one-day (12 hr) injections of three different tracers (ortho-perfluorodimethylcyclohexane (o-PDCH), perfluorotrimethylcyclohexane (PTCH), and perfluorodimethylcyclobutane (PDCB) were injected into the carbon dioxide at the depleted oil well's head. Each injection comprised five hundred milliliters (mls) of tracer injected over a 12-hour (hr) period via a syringe pump. The syringe pump was motor-driven, and was programmed to deliver tracer at a constant flow rate (0.69 ml/min or 41.6 ml/hr) while matching any slight fluctuations in the carbon dioxide pressure. Inasmuch as the carbon dioxide injection was continuous for many days, a tracer was added in the form of a "slug" containing the particular tracer in liquid form. The molar ratio was $5.17 \times 10^{-6}$ mole (mol) of tracer per mol of carbon dioxide. This is based on approximately 2.13 mol of tracer added over a 12-hour (hr) period when 20 tons of carbon dioxide were injected. The well-head pressure was 1685 psig during the injection of the first tracer. By the time the third tracer was injected, the pressure was 1400 psig. There was good agreement between well-head pressure readings and syringe pump readings.

A matrix of both passive and active monitoring sites (with pumps to recirculate gas in the monitoring holes) were placed in a 600-meter diameter circle around the carbon dioxide injection well. There were 38 monitoring holes, eight of which were active sites. In between tracer injections, three sets of CATs absorbent packets were in the monitoring holes, then removed prior to the next tracer injection. However, no CATs were in the ground during each 12-hour injection of tracer(s). CATS packets were left in the ground as long as 54 days. The packets collected anywhere from zero to 1,000 femtograms ($10^{-15}$) of perfluorinated tracers per packet. As a first approximation, the leak rate of carbon dioxide can be estimated from the amount of tracer(s) detected at the surface or near the surface. According to Equation 2, if 1 mole of PFT is added to 1,000,000 moles of carbon dioxide, and the total surface area is 100,000 times the area probed by the monitoring holes:

Number of mols of $CO_2$ which have leaked=(1,000,000)×(Number of mols of PFT detected)×(100,000)  Equation 2

If $2 \times 10^{-4}$ mol of PFT is detected, $2 \times 10^7$ of carbon dioxide have leaked.

After the CATS were retrieved from the monitoring holes, they were sent to the Brookhaven National Laboratory Tracer Technology Laboratory for thermal desorption and analysis for the tracers at very low detection levels near parts per quadrillion (ppq) in soil gas. The analyses are carried out using gas chromatography and either electron capture detection (ECD) or negative ion-chemical ionization mass spectrometry. The detection methods are sensitive to electronegative elements. Fluorine is the most electronegative element and the ECD response is further elevated when $CF_3$ groups are present. $CF_3$ groups are abundantly present in the PFTs.

Figure 6:
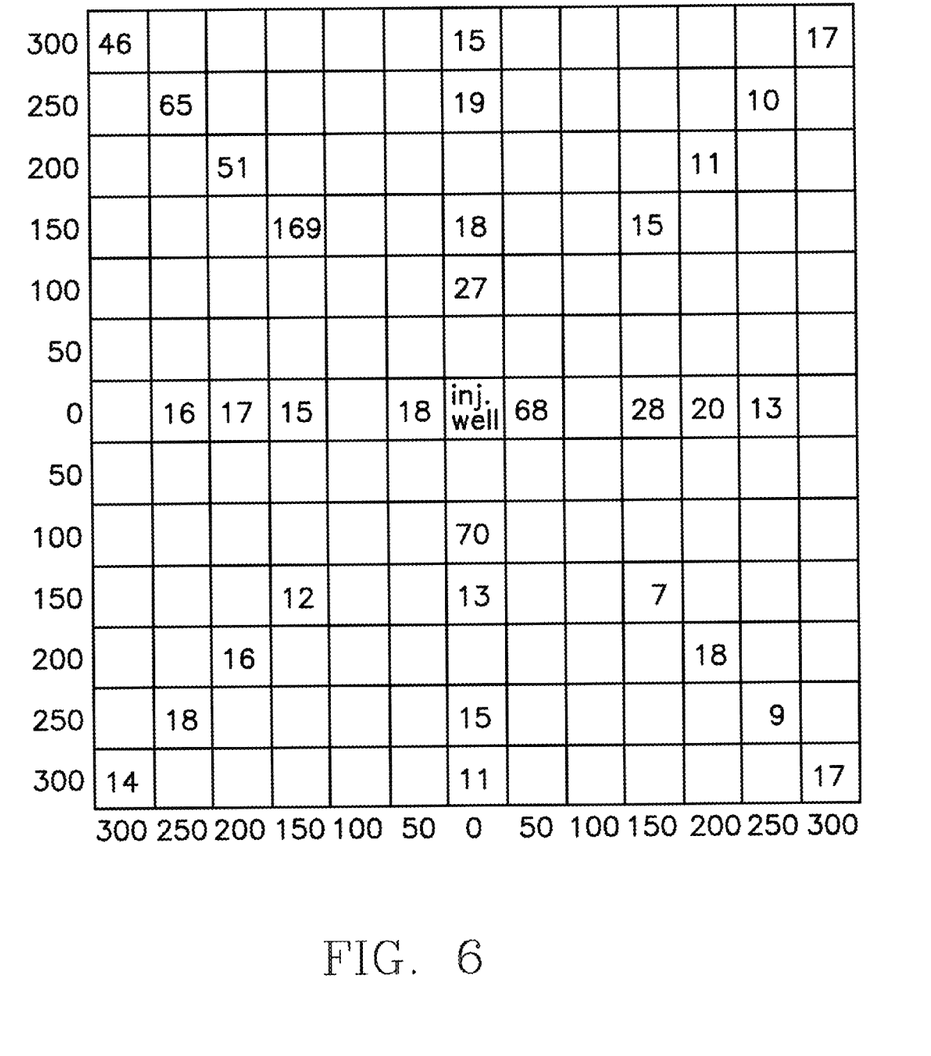
FIG. 6 is a grid graph which depicts the results for passive monitoring sites for one injection of perfluorodimethylcyclohexane (PDCH) into an injection well at a carbon dioxide sequestration site.

FIG. 6 depicts the results for this example for the passive monitoring sites and the third injection of perfluorodimethylcyclohexane (PDCH) in the form of a grid graph. Both the abscissa (x-axis) and the ordinate (y-axis) are centered at the injection well (inj. well). Both axes run from 0 meters (m) to 300 m for both directions on each axis. The numbers given in particular boxes indicate the amount of tracer found at each passive monitoring hole in $10^{-13}$ liter (L), e.g., in the upper left-hand corner of FIG. 6, "46" means $46 \times 10^{-13}$ L of PDCH came out of that monitoring hole.

Tracer Analysis Protocol

A chromatograph run sequence is prepared on an analysis computer (sampling site number and sorbent tubes in order of analysis). The tubes are then loaded onto the carousel of a desorption unit (for desorption of CATS sorbents and GC analysis). Typically, samples from one sampling station for one run (24 tubes and 1 or 2 tubes for background gas analysis), one standard tube every 6 tubes, and a blank tube are analyzed in one analytical run of about 10 hours. The analysis is carried out to determine the total tracer concentration in each sample.

Using the peak height on the chromatogram and the peak height for the most recently run standard (typically perfluoromethylcyclohexane), the amount of sampled PFT, in femtoliters (fL) is obtained. The raw concentration in femtoliters/Liter (fL/L) is calculated by dividing the amount of sampled PFT by the sample volume (27, 36, or 90 liters, depending on the sampler).

Concentration values are adjusted based upon measurement of the tracer content in soil gas at the site before carbon dioxide injection. Typically, this value is very low. A linear interpolation of tracer background levels in soil gas across the monitoring sites is applied to obtain an estimated tracer background level in soil gas. Concentration values are adjusted by multiplying them by the ratio of the PFT concentration in the sample to the assumed invariant PFT background concentration in soil gas.

Leak Mechanisms

Evidence was found for both a diffusive leak mechanism and for the concentration of leakage along shallow surface faults. As such, the invented process detects leaks, and the types of leaks from a sequestration site.

High average concentrations of tracers in soil gas were consistently found in all directions within 100 meters of an injection well in New Mexico, thus giving strong evidence of the injection well bore as the source of the leak. A diffusive pattern was observed with the highest concentrations nearest the injection well bore. Directional high tracer concentrations were also observed, principally to the northwest, and therefore related to a second transport mechanism.

Similarly, in the case of a sequestration site that employs multiple injection wells where a different tracer is added to each injection well, if one tracer is detected at the surface and the other not detected at the surface, one knows where the leaking carbon dioxide is coming from.

The invention has alternative methods for leak detection. Gas accumulation chambers or the modified Li-Cor instrument can be used via placement in the zone to be monitored. The chambers collect carbon dioxide and other soil gases which can have different isotopic composition than does the sequestered carbon dioxide. The chambers also can be used to collect methane, both the methane displaced by sequestered carbon dioxide and the methane produced by methaneogenic bacteria, as well as ethane and propane. Subterranean methane is found in coal formations, depleted gas reservoirs, depleted oil wells, and other geological formations including deep saline aquifers.

The methods herein can be applied to any geologic formation being used for carbon dioxide sequestration, including, but not limited to, active and depleted oil and gas fields, natural gas hydrates, coal beds, brine aquifers, shale formations, and salt domes.

The time span between the injection of carbon dioxide and tracers into the well, and when tracer is first detected at the surface can be an indication of the degree of fracture or microfractures in the rock strata. This information can provide an indication of the flow rate from the sequestration formation to the surface and would thus be useful for geologic studies.

The invention provides a process for the verification of barrier integrity for $CO_2$ sequestration by the monitoring of the leak rate of methane, ethane, and propane and separately, radon (Rn), from the sequestration reservoirs. All of these gases are displaced from underground formations by carbon dioxide.

The invention also provides a process for the sampling and measurement of methane and carbon dioxide in soil gases to differentiate between carbon dioxide and methane coming from near the surface and carbon dioxide being sequestered.

Great sensitivity is provided by the use of PFT tracers inasmuch they are detectable at extremely low concentrations. Furthermore, concentration levels of the PFT tracers are unaffected by atmospheric gases.

Only very minute quantities of the PFT tracers are needed for carbon dioxide leak detection, thus aiding in lower operational costs.

The invention has alternative indicators for leak detection. Methane, ethane, and propane gas displaced by injected carbon dioxide into a sequestration site can serve as an indicator of carbon dioxide leakage. Radon gas can serve the same purpose as methane, ethane, and propane.

The invention further provides a method for branding sequestered carbon dioxide with regard to ownership by injecting a predetermined and registered mixture of perfluorocarbons into sequestered carbon dioxide.

Atmospheric Monitoring

Atmospheric tracer plume monitoring permits the application of a stepwise decision point protocol which leads to a dramatic reduction in actual monitoring costs. In commercial scale sequestration, leakages are rare events if the site was well chosen. Weekly or monthly monitoring activities could consist of single flights by small unmanned aerial vehicles (UAV) carrying sorbent packets. UAV flights are executed by preprogrammed remote computer control, and involve real time communication between a GPS unit on the UAV, ground control and a ground based weather station. The UAV flight plan would be based upon an atmospheric model programmed into the control center.

UAV air sampling protocol incorporates large area integration with continuous extended sweeps at high sampling rates, spot monitoring of areas where terrain or weather conditions might indicate the potential accumulation of atmospheric tracer, and spot monitoring adjacent to areas or features with greater than average leakage potential, such as nearby wells and fault zones. As a general rule, sampling locations higher off the ground will allow for the integration of leakage over larger areas, while lower monitoring elevations will favor better detection. Specific locations of greater leakage potential would be monitored at lower elevations.

Figure 7:
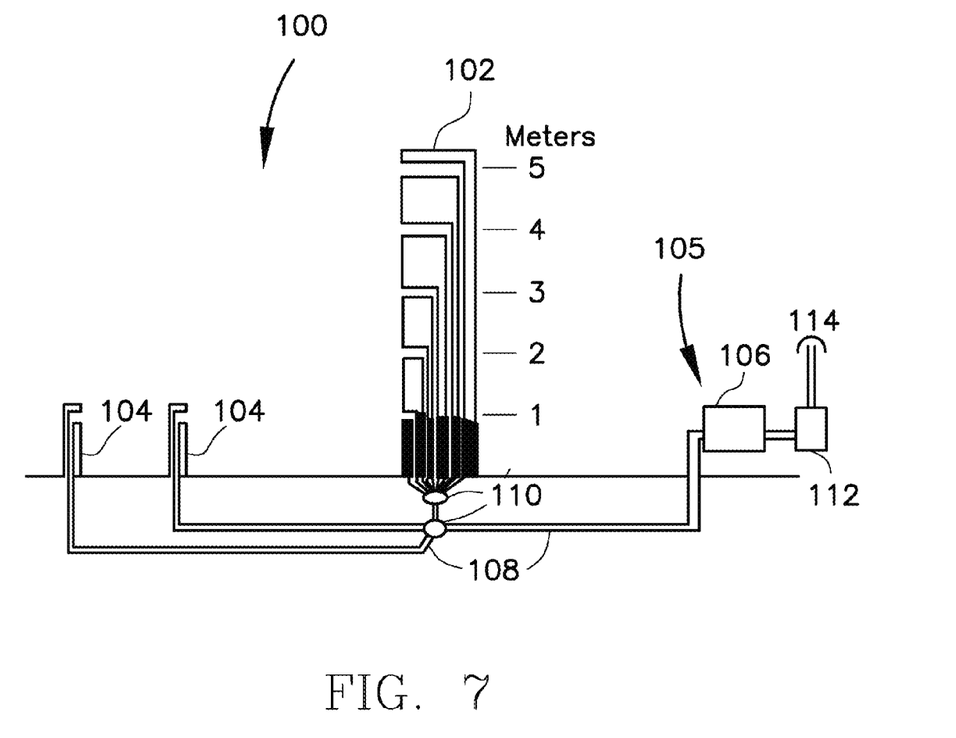
FIG. 7 depicts an automated ground based PFC air sampling system.

Ground based atmospheric tracer monitoring stations are also used. These stations are typically located 4 feet above the surface as shown in FIG. 7. They can conveniently be located on buildings or other structures, or can be located on free standing pipes or portable tripods. The location of these monitors is determined by evaluation of an atmospheric model. The control center computer and model software are in real time communication and together determine which monitoring stations will need to be sampled and when sampling should be conducted. While ground based monitoring will involve more samples to be collected and analyzed than for UAV based monitoring, the number of sorbent packets needed for routine monitoring will still be less than 10% of that required for tracer in soil-gas monitoring. A variation of ground based atmospheric tracer plume monitoring involves the use of towers that can sample vertically at 1 meter intervals up to 4-5 meters. The towers use tubing to sample at various elevations, with the air pump and automatic multisorbent tube sampler located at the base for easy exchanges or automated analysis. Most sequestration sites would require at least 3 such towers, with the control center computer and atmospheric model software controlling which towers would be activated, and when.

FIG. 7 shows an automated ground based PFC tracer air sampling system 100. The tower 102 is 5 meters high, and would be one of 3-6 such towers. Two of many horizontal air monitoring stations 104 are shown in FIG. 7. Both vertical and horizontal monitoring stations are connected to an analytical system 106 by way of tubing 108 and switching valves 110. Air samples are drawn into the analytical system 106 by way of an air pump 112 with vent 114. The tubing is of small diameter and will accommodate pumping rates of 3 liters of air per minute. The horizontal monitors 104 are portable, and can be quickly disconnected from tubing 108 and relocated. The entire analytical unit 105 is portable, and can be moved to a convenient location adjacent to the horizontal monitors 104.

Figure 8:
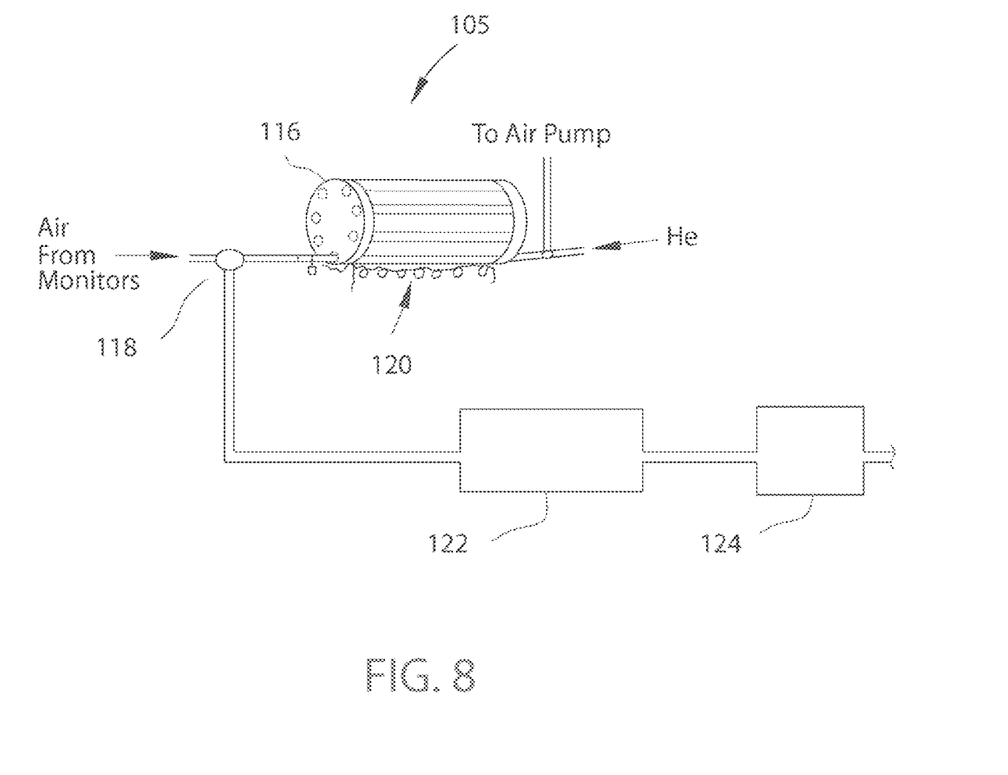
FIG. 8 depicts the analytical portion of the sampling system.

FIG. 8 shows the analytical unit 105. Air from the monitors is fed into a carousel 116 through switching valve 118, and any tracer in the air is adsorbed onto one of several sorbent packets shown in the carousel. After all of the sorbent packets in the carousel have been exposed, tracer on the packets is desorbed by heating with a coil 120, and carried into a gas chromatograph 122 using helium carrier gas. The output of the gas chromatograph 122 is delivered to a negative ion mass spectrometer 124 for detection and quantification of the tracer concentration in sampled air.

Figure 9:
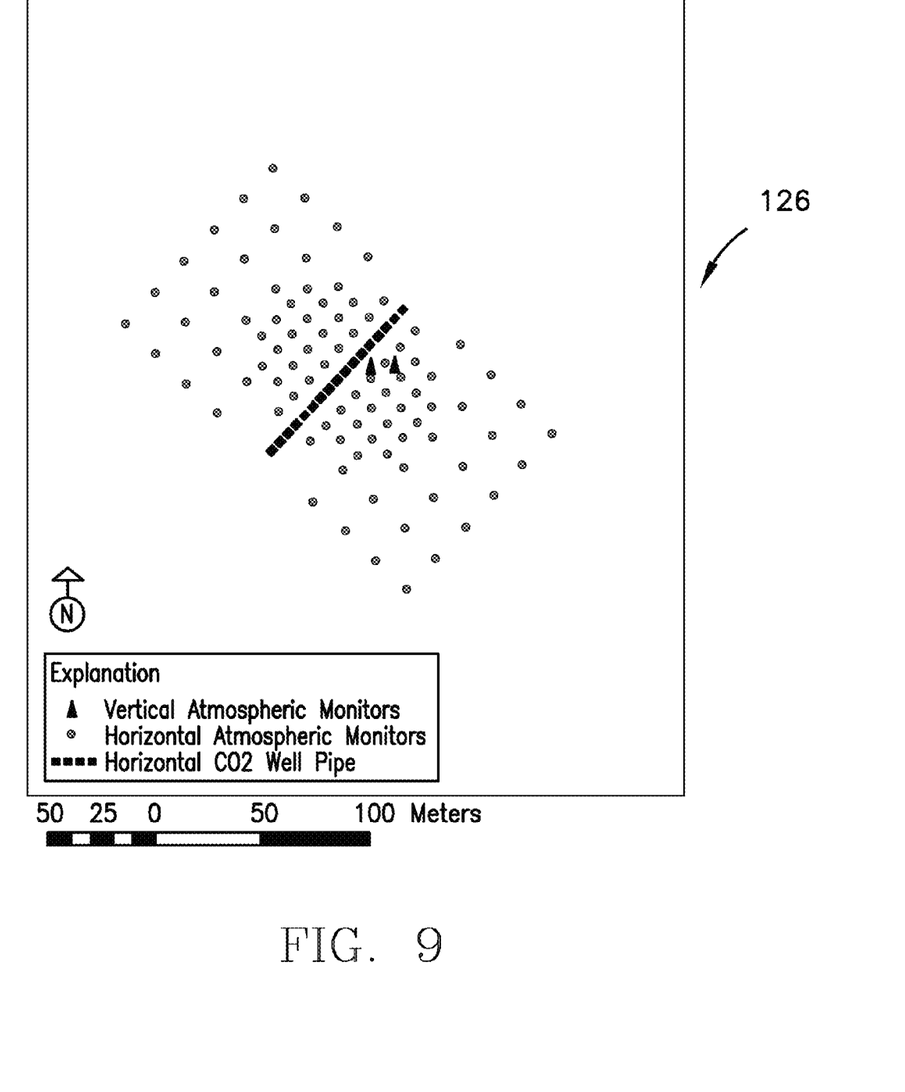
FIG. 9 depicts a ground based monitoring grid.

FIG. 9 shows the design of the ground based monitoring grid (i.e. location of 102 and 104 shown in FIG. 7) based upon the automated evaluation preformed by the central control unit with atmospheric modeling software. Evaluation of ground based monitoring grids has been done at field sites where the deliberate, controlled release of CO2 containing tracers is monitored with ground based atmospheric grids such as 104 in FIG. 7. The grid shown in FIG. 9 is actually 3 superimposed grids with spacings of 40, 20 and 10 meters on a side. Also shown in FIG. 9 are two vertical arrays with sampling towers at 1 meter intervals up to 4 meters. The purpose of these experiments will be to select and evaluate specific grid designs for the completion of Steps 1, 2, and 3 of the sampling protocol. Single atmospheric ground based monitors are also placed adjacent to all potential leakage locations to monitor atmospheric tracer plumes that might be emanating from them. The number of monitoring locations used at sequestration sites would be much less than the number shown in FIG. 9, with portable monitors used in widely spaced arrays, course arrays in one area section of the field at a time and in successively finer arrays around identified source(s) of the tracer plume(s).

Collection of sorbent packets could also be done by hand with analysis in a nearby laboratory. Alternatively a system of tubing could deliver air samples from a horizontal sampling grid to a central laboratory.

The Department of Energy has established a goal of no more than a 10% increase in the expense of industrial processes associated with sequestration monitoring activities. Atmospheric tracer plume monitoring is well suited to a stepwise decision point monitoring protocol that would significantly reduce the cost of near surface monitoring.

The protocol involves:
Step 1 Primary Detection Surveys
Step 2 Conformation Surveys i.e. more intensive sector surveys
Step 3 Plume Source Identification Surveys Obtaining better statistics to reduce false positives, and a more complicated terrain or weather pattern may require the exposure of more sorbent packets in Step (1), but the numbers and expense will be less than 10% of that required for tracer in soil-gas monitoring. Step (2) would be activated following 2 consecutive UAV flights showing tracer levels significantly about background levels based upon positive results for 2 or 3 of the sorbent packets in Step (1). Step (2) would also be activated based upon similar results for 2 consecutive ground based monitoring surveys. Step (2) would consist of finer spaced UAV sweeps, or the activation of ground based monitoring locations that are normally inactive, or the placement of portable monitors. Step (2) monitoring would likely be conducted in stages to monitor individual sectors of the sequestration site. Once positive confirmation of leakage was established, and likely leakage source candidates identified, then Step (3) would be initiated to locate the exact source of the tracer plume. Step (3) will require a substantial investment in time and resources but even here, costs could be reduced by using automated systems. Step (3) involves using a series of successively finer UAV sweeps, or of successively finer horizontal/vertical atmospheric ground based grids. Individual sweeps or grids would be used to quantify atmospheric tracer gradients for the correct placement of the next finer sweep or grid. It is not anticipated that Step (3) would ever be activated during commercial sequestration operations, but practice runs at release test sites will be used to confirm the integrity of the monitoring protocol and techniques.

This technique represents a significant improvement over the current state-of-the-art technique for atmospheric CO2 plume monitoring, which is the eddy covariance method. The major limitation of eddy covariance is that is often impossible to distinguish a relatively weak CO2 leakage plume from the numerous natural background sources. Since the current invention detects introduced tracers rather than measuring CO2 directly, the background levels are usually negligible. Therefore, the sensitivity of this invention is significantly higher.

Monitoring in Shallow Aquifer Water Samples

In addition to atmospheric plume and soil-gas monitoring, another useful approach to monitoring for PFC tracers in the near surface is to look for their appearance in samples of shallow water aquifers that drain the immediate vicinity of the sequestration site. The EPA has already determined that a careful evaluation of the possible infusion of sequestered $CO_2$ into shallow, portable water aquifers will be conducted as part of any sequestration monitoring program. Both atmospheric tracer plume monitoring and shallow aquifer monitoring have the advantage of integrating leakage over specified areas. The drainage area monitored can be controlled by the careful placement of monitoring water wells in the context of local surface hydrology. The entire area above the $CO_2$ plume in the target reservoir can be monitored by selecting sites at the appropriate distance from the sequestration site, and in the direction of the hydrologic down-gradient, while up-gradient water well monitors can be used as a control. Higher levels of detection sensitivity can be achieved by also monitoring closer to specific locations of greater leakage potential, such as wells that intercept the target reservoir, and near fault zones. This is analogous to sampling the air at higher elevations, and further down wind from a potential atmospheric tracer release zone to increase the area of integration.

Wells in freshwater aquifers are much less expensive to construct than monitoring wells sent to reservoir depth. The tracers are non-toxic, and are a small component of the sequestered $CO_2$ hence would be much less of an environmental concern than the $CO_2$ itself or than other PFCs present in the environment at much higher levels like perfluorooctane sulfonate (PFOS). PFCs currently remain below the "predicted no-effect concentration" value in the environment. Monitoring for tracers in shallow well waters would have little effect on the cost of pre-existing water monitoring programs.

The current standard approach to water monitoring is to monitor for chemical changes in sampled waters from pre-injection background levels. In addition to monitoring properties such as pH and alkalinity, changes in cations and anions are taken to reflect reactions of $CO_2$ with clays and other minerals that are in contact with the aquifer. There is, however, currently no method available to distinguish the infusion of injected $CO_2$ into shallow aquifers from biogenic sources (and sinks) at levels required for monitoring. The sensitivity of the current approach to small levels of $CO_2$ infusion may be lost in a number of ways: (1) seasonal variations in the background levels of $CO_2$ may be very large, especially in areas with dense vegetation, (2) the levels of $CO_2$ infusion required to produce detectable levels of change in water chemistry is quite high, and (3) even a year long background survey may not reflect post-injection years due to meteorological changes that can effect the growth and decay rate of vegetation, and the levels of microbiological activity. The use of tracers will greatly reduce the influence of these variables, will significantly lower the level of injected $CO_2$ that can be detected in water samples, and will complement any already existing shallow aquifer monitoring program at little additional cost.

Aliquots of water samples that have not been acidified or otherwise treated are taken for the analysis of PFC tracers along with samples taken for other analysis. Analysis is conducted via GC with negative ion mass spectrometer detection. An automated, headspace sampling system is employed that first heats the 20-30 ml water samples to 80 C. Pre-concentration of tracers by liquid/liquid extraction or other extraction procedures can be conducted if needed to achieve lower detection limits. Sealing monitoring water wells will allow tracer concentrations, if present, to build up in the headspace above the water. This headspace can then be sampled periodically and analyzed for PFC tracers.

While the invention has been described with reference to details of the illustrated embodiment, these details are not intended to limit the scope of the invention as defined in the appended claims.

The embodiment of the invention in which an exclusive property or privilege is claimed is defined as follows:

1. A method for the measurement of carbon dioxide leakage rate from sequestration reservoirs, the method comprising:
    A). Adding tracer molecules selected from the group of sulfur containing compounds, halogen containing compounds, hydrocarbon compounds, perfluorocarbon compounds and inert gases to carbon dioxide at a predetermined molar ratio;
    B). Allowing the tracer molecules and carbon dioxide to mix homogeneously;
    C). Injecting the homogenous mixture of tracer molecules and carbon dioxide into sequestration reservoirs;
    D). Collecting leaked tracer molecules onto a sorbent during a known time period onto sorbents specific for retaining the tracer molecules at or near injection points, fracture zones, formation outcroppings, areas around an underground carbon dioxide plume soil atmosphere interface, aerial collection towers, unmanned aerial vehicles and freshwater aquifers and wells; and,
    E). Measuring concentrations of both the collected tracer molecules and carbon dioxide to determine the rate of carbon dioxide leakage over a period of time.

2. The method as recited in claim 1 wherein a plurality of tracers are added simultaneously to the carbon dioxide.

3. The method as recited in claim 1 wherein the tracers and the carbon dioxide are injected in a tracer to carbon dioxide molar ratio of at least $1 \times 10^{-6}6:1$.

4. The method as recited in claim 1 wherein the overall sequestration reservoir leak rate is calculated using both the tracer concentration measurements and a measured increase on $CO_2$ surface flux rate in soil and surface gases after sequestration.

5. The method as recited in claim 1 wherein the collected tracer molecules are passed through a tube containing sorbent specific to the gas to be analyzed and confined for a period of time to the sorbent for analysis.

6. The method as recited in claim 4 wherein the soil and surface gases are methane ($CH_4$) and carbon dioxide ($CO_2$).

7. The method as recited in claim 1 wherein the tracer molecules are selected from a group consisting of methane, ethane, propane, carbon tetrafluoride, hexafluorethane, sulfur hexafluoride, carbon-13 labeled carbon dioxide, carbon disulfide, and molecules containing perfluoro functional groups.

8. The method as recited in claim 1 wherein the location of a leak at the surface is determined by laying out a grid of surface monitoring sites and determining the leak rate at each site.

9. The method as recited in claim 1 wherein the tracers are selected to provide a chemical signature for each reservoir.

* * * * *